US008241765B2

(12) United States Patent
Barbera-Guillem

(10) Patent No.: US 8,241,765 B2
(45) Date of Patent: Aug. 14, 2012

(54) FLUORESCENT INK COMPOSITIONS COMPRISING FUNCTIONALIZED FLUORESCENT NANOCRYSTALS

(75) Inventor: Emilio Barbera-Guillem, Powell, OH (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 12/844,816

(22) Filed: Jul. 27, 2010

(65) Prior Publication Data
US 2011/0101240 A1 May 5, 2011

Related U.S. Application Data

(63) Continuation of application No. 10/884,528, filed on Jul. 2, 2004, now Pat. No. 7,785,717, which is a continuation of application No. 10/417,303, filed on Apr. 16, 2003, now Pat. No. 6,835,326, which is a continuation of application No. 09/755,407, filed on Jan. 5, 2001, now Pat. No. 6,576,155, which is a continuation-in-part of application No. 09/436,145, filed on Nov. 9, 1999, now abandoned, which is a continuation-in-part of application No. 09/372,729, filed on Aug. 11, 1999, now Pat. No. 6,114,038.

(60) Provisional application No. 60/107,829, filed on Nov. 10, 1998.

(51) Int. Cl.
*B32B 9/00* (2006.01)
*B32B 19/00* (2006.01)
(52) U.S. Cl. ..................................... 428/690; 428/195.1
(58) Field of Classification Search .................. 428/690, 428/195.1
See application file for complete search history.

(56) References Cited

U.S. PATENT DOCUMENTS

| | | |
|---|---|---|
| 4,150,997 A | 4/1979 | Hayes |
| 4,153,593 A | 5/1979 | Zabiak et al. |
| 4,767,205 A | 8/1988 | Schwartz et al. |
| 5,194,300 A | 3/1993 | Cheung |
| 5,194,305 A | 3/1993 | Shirahata et al. |
| 5,256,395 A | 10/1993 | Barbet et al. |
| 5,289,547 A | 2/1994 | Ligas et al. |
| 5,478,381 A | 12/1995 | Ohiwa et al. |
| 5,580,923 A | 12/1996 | Yeung et al. |
| 5,592,561 A | 1/1997 | Moore |
| 5,623,001 A | 4/1997 | Figov |
| 5,637,258 A | 6/1997 | Goldburt |
| 5,733,971 A | 3/1998 | Feldmann-Krane et al. |
| 5,747,349 A | 5/1998 | Van den Engh et al. |
| 5,751,018 A | 5/1998 | Alivisatos et al. |
| 5,755,860 A | 5/1998 | Zhu |
| 5,756,685 A | 5/1998 | Fritzberg et al. |
| 5,786,219 A | 7/1998 | Zhang et al. |
| 5,795,379 A | 8/1998 | Schwenk et al. |
| 5,837,042 A | 11/1998 | Lent et al. |
| 5,882,779 A | 3/1999 | Lawandy |
| 5,939,468 A | 8/1999 | Siddiqui |
| 5,990,197 A | 11/1999 | Escano et al. |
| 5,990,479 A | 11/1999 | Weiss et al. |
| 6,114,038 A | 9/2000 | Castro et al. |
| 6,179,912 B1 | 1/2001 | Barbera-Guillem et al. |
| 6,207,392 B1 | 3/2001 | Weiss et al. |
| 6,251,303 B1 | 6/2001 | Bawendi et al. |
| 6,426,513 B1 | 7/2002 | Bawendi et al. |
| 6,444,143 B2 | 9/2002 | Bawendi et al. |
| 6,458,294 B2 | 10/2002 | Oshima et al. |
| 6,514,446 B1 | 2/2003 | Smith et al. |
| 6,565,770 B1 | 5/2003 | Mayer |
| 6,572,784 B1 | 6/2003 | Coombs et al. |
| 6,575,155 B2 | 6/2003 | Brennan |
| 6,692,031 B2 | 2/2004 | McGrew |

FOREIGN PATENT DOCUMENTS

WO WO-00/29617 5/2000

OTHER PUBLICATIONS

"Quantum Dot" as defined from Wikipedia, Jul. 8, 2009.
Final Office Action for U.S. Appl. No. 10/884,528 mailed on Jul. 20, 2006.
Final Office Action for U.S. Appl. No. 10/884,528 mailed on Apr. 30, 2008.
Non-Final Office Action for U.S. Appl. No. 10/884,528 mailed on Feb. 22, 2006.
Non-Final Office Action for U.S. Appl. No. 10/884,528 mailed on Oct. 24, 2006.
Non-Final Office Action for U.S. Appl. No. 10/884,528 mailed on Sep. 4, 2007.
Office Action for U.S. Appl. No. 10/884,528 mailed Jan. 4, 2010.
Office Action for U.S. Appl. No. 10/884,528 mailed Jul. 8, 2009.
Response to Apr. 30, 2008 Final Office Action in U.S. Appl. No. 10/884,528, filed Oct. 30, 2008.
Response to Jul. 20, 2006 Final Office Action in U.S. Appl. No. 10/884,528, filed Sep. 20, 2006.
Response to Sep. 4, 2007 Non-Final Office Action in U.S. Appl. No. 10/884,528, filed Feb. 4, 2008.
Response to Oct. 24, 2006 Non-Final Office Action for U.S. Appl. No. 10/884,528, filed Nov. 30, 2006.
Response to Feb. 22, 2006 Non-Final Office Action for U.S. Appl. No. 10/884,528, filed May 19, 2006.
Notice of Allowance for U.S 884,528 mailed Apr. 26, 2010.
Bruchez Jr., M., et al. "Semiconductor Nanocrystals as Fluorescent Biological Labels", *Science*, 281:1998, p. 2013-2016.
Castro, Stephani "BioPixel nanocrystalline fluorescent markers", *Genetic Engineering News* vol. 19, No. 17 Oct. 1, 1999, 28-29. Chan, W., et al. "Quantum Dot Bioconjugates for Ultrasensitive Nonisotopic Detection", *Science* 281:1998, p. 2016-2018.
Dabbousi, B., et al. "(CDSE)ZnS Core—Shell Quantum Dots: Synthesis and Characterization of a Size Series of Highly Luminescent Nanocrystallites", *Journal of Physical Chemistry*, 101: 1997, p. 9463-9475.
Danek, M., et al. "Synthesis of Luminescent Thin-Film CdSe/ZnSe Quantum dot composites Using CdSe Quantum Dots Passivated with an Overlayer of ZnSe", *Chemistry of Materials* 8(1):1996, p. 173-180.
Efros, A., et al. "Band-edge exciton in quantum dots of semiconductors with a degenerate valence band: dark and bright exciton states", *Physical Review B*. 54 (7): 1996, p. 4843-4856.
Emory, S., et al. "Direct Observation of Size-Dependent Optical Enhancement in Single Metal Nanoparticles", *Journal of the American Chemical Society* 120 (31): 1998, p. 8009-8010.

(Continued)

*Primary Examiner* — Betelhem Shewareged
(74) *Attorney, Agent, or Firm* — Life Technologies Corporation

(57) ABSTRACT

A fluorescent ink composition comprising functionalized fluorescent nanocrystals, an aqueous-based ink carrier comprising water or a water-based solution, and a binder. Also provided are methods of providing an image or a security mark on a substrate for subsequent identification by applying a fluorescent ink composition onto the substrate.

10 Claims, 1 Drawing Sheet

OTHER PUBLICATIONS

Empedocles, S., et al. "Photoluminescence Spectroscopy of Single CdSe Nanocrystallite Quantum Dots", *Physical Review Letters* 77(18): 1996, p. 3873-3876.

Jacoby, M. "Quantum Dots Meet Biomolecules", *Chemical & Engineering News* 76 (39): 1998, p. 8.

Murakoshi, K., et al. "Control of Surface Coverage and Solubility of Thiophenolate-Capped CdS Nanocrystallites", *J. Colloid Interface Sci.*, 203:1998, p. 225-228.

Murray, C., et al. "Self-Organization of CdSe Nanocrystallites into Three-Dimensional Quantum Dot Superlattices", *Science* 1995, p. 1335-1338.

Murray, C., et al. "Synthesis and characterization of nearly monodisperse CdE (E= sulfur, selenium, tellurium) semiconductor nanocrystallites", *Journal of the American Chemical Society* 115 (19): 1993, p. 8706-8715.

Nirmal, M., et al. "Fluorescence Intermittency in Single Cadmium Selenide Nanocrystals", *Nature, Nature Publishing Group*, London, UK 383:1996, p. 802-804.

Norris, D., et al. "Measurement and Assignment of the Size-Dependent Optical Spectrum in CdSe Quantum Dots", *Physical Review B*. 53 (24): 1996, p. 16338-16346.

International Search Report for PCT Application No. PCT/US01/16678 mailed Aug. 28, 2001.

International Search Report for PCT Application No. PCT/US01/17912 mailed Oct. 11, 2001.

International Search Report for PCT Application No. PCT/US01/49441 mailed May 28, 2002.

Peng, X., et al. "Epitaxial growth of highly luminescent Cdse/cdS core/ Shell Nanocrystals with photostability and electronic accessibilty", *J. Am. Chem. Soc.*, 119: 1997, p. 7019-7029.

Rodriguez-Viejo, J., et al. "Cathodoluminescence and photolumincesence of highly luminescent CdSe/ZnS quantum dot composites", *Appl. Phys. Lett*. 70 (16): 1997, p. 2132-2134.

Sacra, A., et al. "Stark spectroscopy of CdSe nanocrystallites: The significance of transition linewidths",*J. Chem. Phys*. 103(13):1995, p. 5236-5245.

Service, R. "Semiconductor Beacons Light Up Cell Structures", *Science* vol. 281:1988, p. 1930-1931.

FLUORESCENT INK COMPOSITIONS COMPRISING FUNCTIONALIZED FLUORESCENT NANOCRYSTALS

CROSS-REFERENCE TO RELATED APPLICATIONS

This application is a continuation of U.S. patent application Ser. No. 10/884,528, filed Jul. 2, 2004, now U.S. Pat. No. 7,785,717, which is a continuation of U.S. patent application Ser. No. 10/417,303, filed Apr. 16, 2003, now U.S. Pat. No. 6,835,326, which is a continuation of U.S. patent application Ser. No. 09/755,407, filed Jan. 5, 2001, now U.S. Pat. No. 6,576,155, which is a continuation-in-part of U.S. patent application Ser. No. 09/436,145, filed Nov. 9, 1999, now abandoned, which is a continuation-in-part of U.S. patent application Ser. No. 09/372,729, filed Aug. 11, 1999, now U.S. Pat. No. 6,114,038, which claims priority to and the benefit of U.S. Provisional Application Ser. No. 60/107,829, filed Nov. 10, 1998, the disclosures of which are herein incorporated by reference in their entirety.

FIELD OF THE INVENTION

This invention relates to water-based printing inks; and more particularly to fluorescent ink compositions useful in various printing methods such as ink jet printing.

BACKGROUND OF THE INVENTION

Ink jet printing is a standard and preferred method for printing onto a substrate, wherein a stream of ink droplets are directed from a printing device to a surface of the substrate. The direction of the stream is controlled electronically in causing the droplets to print the desired image or information on the substrate surface without requiring contact between the printing device and the surface to which the ink is applied. Ink jet printing may be applied to a variety of substrates including, but not limited to, metals, glass, synthetic resins, plastics, rubber, paper, and the like. Objects, comprising substrates to which ink jet printing is well suited, include, but are not limited to, containers for consumer products, currency, draft checks, envelopes, letterhead, identification cards, bank cards (debit, credit, and the like), identification strips (e.g., comprising barcodes), and the like.

Fluorescent inks have been developed for printing a "security mark" on articles such that the mark is invisible to the unaided eye, but that can be detected as fluorescence upon excitation with an activating light of a suitable excitation wavelength spectrum. More particularly, security marks are applied to articles in efforts to prevent forgery, theft, and fraud; wherein such articles are known to include, but are not limited to, identification cards, passports, currency, checks, securities, and other types of commercial paper. The security mark may be in the form of a barcode which encodes information, or may comprise a recognizable pattern for identification and verification purposes. Prior art fluorescent inks are known in the art to include: a fluorescent colorant, a solvent, and a binder resin; an organic laser dye that is excited by a wavelength spectrum in the near infrared range and fluoresces in an infrared range; a phenoxazine derivative dye fluorescing in the near infrared range; a rare earth metal, an organic ink carrier, and may further comprise a chelating agent; and a near infrared fluorophore and a water-dissipatable polyester. Generally, such fluorescent inks comprising fluorescent dyes or pigments, present with several disadvantages. For example, there is a relatively narrow margin between the amount of a fluorescent dye which is sufficient to give good fluorescent color intensity, and an amount wherein the dye molecules begin to aggregate and thus reduce the amount of fluorescence by quenching. A limitation in intensity can also limit the density of information encoded on a security mark (such as a barcode) by a fluorescent ink composition.

Thus, there exists a need for fluorescent ink compositions suitable for printing on substrates, wherein (a) the fluorescent component of the fluorescent ink composition is water-soluble; (b) the fluorescent component is excited by a wavelength spectrum comprising UV light, and preferably in a spectral range of from about 300 nanometers (nm) to about 400 nm, and emits an narrow emission peak in a wavelength spectrum primarily in the visible range, and preferably in a spectral range of from about 410 nm to about 750 nm; (c) a plurality of fluorescent ink compositions (each containing a fluorescent component that can be detectably distinguished (e.g., by fluorescent color and/or intensity) from that of other fluorescent ink compositions of the plurality of fluorescent ink compositions) may be utilized for multicolor fluorescence by excitation with a single wavelength spectrum of light resulting in simultaneous detection of fluorescence of high quantum yield and with discrete peak emission spectra; (d) a fluorescent component that resists photobleaching (and therefore can be used for signal integration); and (e) a fluorescent component that is not susceptible to quenching.

SUMMARY OF THE INVENTION

Provided are fluorescent ink compositions comprising a fluorescent component that comprises functionalized fluorescent nanocrystals (e.g., a single type for print of a single fluorescent color, or a plurality of types for print of multicolor), an ink carrier, and a binder; and may further comprise other components such as one or more of a biocide, a surfactant, a defoamer, and the like. One or more fluorescent ink compositions are printed onto the surface of a substrate using a printer device. Following excitation of the printed surface with an appropriate excitation wavelength spectrum, each of the one or more fluorescent ink compositions printed on the surface will emit fluorescence of high quantum yield and with discrete peak emission. The fluorescent ink composition may be varied with respect to the intensity of fluorescence emission. Variables such as differences in intensity and in fluorescent color can enable an increase in the information that can be stored in a security mark, as well as increase the possible number and complexity of a security mark so as to prevent forgery. For example, the fluorescent ink composition can be varied by controlling the amount and type of functionalized fluorescent nanocrystals in the method of preparing the fluorescent ink composition. Thus, the fluorescent properties of the fluorescent ink composition, such as intensity and color, are sensitive to the functionalized fluorescent nanocrystals made apart thereof. A resultant advantage of the fluorescent ink compositions of the present invention is that they may be produced to have a greater degree of fluorescence (intensity) than previously known fluorescent jet compositions.

An additional advantage of the use of the fluorescent ink compositions according to the present invention relates to the use of a plurality of the fluorescent ink compositions in printing a desired pattern onto a surface. Each fluorescent ink composition may be comprised of a type of functionalized fluorescent nanocrystals capable of fluorescing a specific color. Thus, the plurality of fluorescent ink compositions maybe used to print a desired pattern which be excited to emit multicolor fluorescence which may be visible simultaneously in generating a specific, identifiable code (based on the emission spectra which can comprise both color and intensity) that can be used for purposes of verification or identification. For example, a plurality of fluorescent ink compositions may comprise a first ink composition capable of fluorescing red, a second ink composition capable of fluorescing blue, a third ink composition capable of fluorescing yellow, and a fourth composition capable of fluorescing green. This exemplary combination of a fluorescent ink compositions may be used to print currency with a security mark comprising a code (based on the number, or number and intensity, of colors) for verification purposes. Further, in a method of producing the fluorescent ink composition according to the present invention, by controlling the proportion of the components, precise control may be achieved with respect to the basic fluorescent properties of the resultant fluorescent ink composition.

The above and other objects, features, and advantages of the present invention will be apparent in the following Detailed Description of the Invention.

DETAILED DESCRIPTION OF THE INVENTION

Definitions

Figure 1A:
FIG. 1A is a schematic illustration of an identifiable code pattern, associated with a card, comprised of separate deposits or localizations of water-soluble quantum dot compounds of different uniform sizes which enable a detectable and identifiable pattern comprised of multiple colors.

By the term "functionalized fluorescent nanocrystals" is meant, for purposes of the specification and claims to refer to nanocrystals comprising semiconductor nanocrystals or doped metal oxide nanocrystals, wherein the nanocrystals are operably bound to, and functionalized by the addition of, a plurality of molecules which provide the functionalized fluorescent nanocrystals with reactive functionalities to enable the fluorescent nanocrystals to be soluble in the aqueous-based ink carrier of the fluorescent ink composition; wherein the plurality of molecules may be selected from the group consisting of carboxylic acid, an amino acid, a diaminocarboxylic acid, a monoaminocarboxylic acid, and a combination thereof. Further, the reactive functionalities may aid the functionalized nanocrystals to become bound to one or more of the binder of the fluorescent ink composition, or the substrate onto which they are applied. A preferred type of molecules to functionalized the fluorescent nanocrystals may be used to the exclusion of molecules other than the preferred type of molecules. The functionalized nanocrystals are sufficiently soluble in an aqueous-based environment provided by an ink carrier in forming an aqueous-based fluorescent ink composition.

By the term "semiconductor nanocrystals" is meant, for purposes of the specification and claims to refer to quantum dots (crystalline semiconductors) comprised of a core comprised of at least one of a Group II-VI semiconductor material (of which ZnS, and CdSe are illustrative examples), or a Group III-V semiconductor material (of which GaAs is an illustrative example), a Group IV semiconductor material, or a combination thereof. In a preferred embodiment, the core of the quantum dots may be passivated with an semiconductor overlayering ("shell") uniformly deposited thereon. For example, a Group II-VI semiconductor core may be passivated with a Group II-VI semiconductor shell (e.g., a ZnS or CdSe core may be passivated with a shell comprised of YZ wherein Y is Cd or Zn, and Z is S, or Se). As known to those skilled in the art, the size of the semiconductor core correlates with the spectral range of emission. Table 1 is an illustrative example for CdSe.

TABLE 1

| Color | Size Range(nm) | Peak Emission Range |
|---|---|---|
| blue | 2.5 to 2.68 | 476 to 486 |
| green | 2.8 to 3.4 | 500 to 530 |
| yellow | 3.58 to 4.26 | 536 to 564 |
| orange | 4.9 to 6.1 | 590 to 620 |
| red | 8.6 to 10.2 | 644 to 654 |

In a preferred embodiment, the semiconductor nanocrystals are produced using a continuous flow process and system disclosed in copending U.S. application Ser. No. 09/468,418 (the disclosure of which is herein incorporated by reference), and have a particle size that varies by less than +/−4% in the average particle size. In a preferred embodiment, the semiconductor nanocrystals comprise a monodisperse population having an average particle size (as measure by diameter) in the range of approximately 1 nanometer (nm) to approximately 20 nm.

By the term "doped metal oxide nanocrystals" is meant, for purposes of the specification and claims to refer to nanocrystals comprised of: a metal oxide and a dopant comprised of one or more rare earth elements. For example, suitable metal oxides include, but are not limited to, yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr_2O_3$), lanthanum oxide ($La_2O_3$), and alloys thereof. The rare earth element comprises an element selected from the Lanthanide series and includes, but is not limited to, europium (Eu), cerium (Ce), neodymium (Nd), samarium (Sm), terbium (Tb), gadolinium (Gd), holmium (Ho), thulium (Tm), an oxide thereof, and a combination thereof. As known to those skilled in the art, depending on the dopant, an energized doped metal oxide nanocrystal is capable of emitting light of a particular color. Thus, the nature of the rare earth or rare earths are selected in consequence to the color sought to be imparted (emitted) by a doped metal oxide nanocrystal used in the fluorescent ink composition according to the present invention. A given rare earth or rare earth combination has a given color, thereby permitting the provision of doped metal oxide nanocrystals, each of which may emit (with a narrow emission peak) a color over an entire range of colors by adjusting the nature of the dopant, the concentration of the dopant, or a combination thereof. For example, the emission color and brightness (e.g., intensity) of a doped metal oxide nanocrystal comprising $Y_2O_3$:Eu may depend on the concentration of Eu; e.g., emission color may shift from yellow to red with increasing Eu concentration. For purposes of illustration only, representative colors which may be provided are listed in Table 2.

TABLE 2

| Fluorescent Color | Dopant |
| --- | --- |
| blue | thulium |
| blue | cerium |
| yellow-green | terbium |
| green | holmium |
| green | erbium |
| red | europium |
| reddish orange | samarium |
| orange | neodymium |
| yellow | dysprosium |
| white | praseodymium |
| orange-yellow | europium + terbium |
| orange-red | europium + samarium |

Methods for making doped metal oxide nanocrystals are known to include, but are not limited to a sol-gel process (see, e.g., U.S. Pat. No. 5,637,258), and an organometallic reaction. As will be apparent to one skilled in the art, the dopant (e.g., one or more rare earth elements) are incorporated into the doped metal oxide nanocrystal in a sufficient amount to permit the doped metal oxide nanocrystal to be put to practical use in fluorescence detection as described herein in more detail. An insufficient amount comprises either too little dopant which would fail to emit sufficient detectable fluorescence, or too much dopant which would cause reduced fluorescence due to concentration quenching. In a preferred embodiment, the amount of dopant in a doped metal oxide nanocrystal is a molar amount in the doped metal oxide nanocrystal selected in the range of from about 0.1% to about 25%. Doped metal oxide nanocrystals may can be excited with a single excitation light source resulting in a detectable fluorescence emission of high quantum yield {e.g., a single quantum dot having at a fluorescence intensity that may be a log or more greater than that a molecule of a conventional fluorescent dye) and with a discrete fluorescence peak. Typically, they have a substantially uniform size of less than 200 Angstroms, and preferably have a substantially uniform size in the range of sizes of from about 1 nm to about 5 nm, or less than 1 nm. In a preferred embodiment, the doped metal oxide nanocrystals are comprised of metal oxides doped with one or more rare earth elements, wherein the dopant comprising the rare earth element is capable of being excited (e.g., with ultra-violet light) to produce a narrow spectrum of fluorescence emission. In another preferred embodiment, the doped metal oxide has both fluorescent properties {when excited with an excitation light source) and magnetic properties. Thus, in one embodiment, a fluorescent ink composition may comprise functionalized fluorescent nanocrystals comprising doped metal oxide nanocrystals which are magnetic.

By the term "operably bound" is meant, for purposes of the specification and claims to refer to fusion or bond or an association of sufficient stability to withstand conditions encountered in a method of detection, between a combination of different molecules such as, but not limited to, between functionalized fluorescent nanocrystals and the binder, and between a fluorescent nanocrystal and the molecules with which it is functionalized (e.g., carboxylic acid, diaminocarboxylic acid, or a monoaminocarboxylic acid), and a combination thereof. As known to those skilled in the art, the bond may comprise one or more of covalent, ionic, hydrogen, van der Waals, and the like. As known to those skilled in the art, and as will be more apparent by the following embodiments, there are several methods and compositions in which two or more molecules may be operably bound utilizing reactive functionalities. Reactive functionalities include, but are not limited to, free chemical groups (e.g., thiol, or carboxyl, hydroxyl, amino, amine, sulfo, etc.), and reactive chemical groups (reactive with free chemical groups).

The term "suitable conditions" is used herein, for purposes of the specification and claims, and with reference to a process of reacting two components (e.g., functionalized fluorescent nanocrystals and a binder), to mean those conditions under which the components may become operably bound to each other. As known to those skilled in the art, such conditions may include one or more of: a pH range of from about 3 to about 9, ionic strengths such as that ranging from distilled water to about 1 molar sodium chloride, and a temperature in the range of from about 4° C. to about 45° C.; and may further include a time sufficient for binding to occur (e.g., in a range of from about 10 minutes to about 2 hours).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, and an amino acid precursor (e.g., citrulline and ornithine are intermediates in the synthesis of arginine). In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Exemplary diaminocarboxylic acids include, but are not limited to, lysine, asparagine, glutamine, arginine, citrulline, ornithine, 5-hydroxylysine, djenkolic acid, β-cyanoalanine, and synthetic diaminocarboxylic acids such as 3,4-diaminobenzoic acid, 2,3-diaminopropionic acid, 2,4-diaminobutyric acid, 2,5-diaminopentanoic acid, and 2,6-diaminopimelic acid.

By the term "amino acid" is meant, for purposes of the specification and claims to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, a seleno group, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, β-alanine, homoserine, γ-aminobutyric acid, and homocysteine. Other preferred amino acids include sulfur containing amino acids (e.g., cysteine, homocysteine, s-allyl-L-cysteine sulfoxide, taurine, penicillamine, and the like); and seleno containing amino acids (e.g., selenocysteine, selenohomocysteine, Semethylselenocysteine, selenocystine, selenohomocystine, and the like).

By the term "carboxylic acid" is meant, for purposes of the specification and claims to refer to a compound having the formula $HS(CH_2)_n X$, wherein X is a carboxylate (carboxylic moiety). "n" is a number in the range of from 1 to about 20, and preferably greater than 4. In a preferred embodiment, the thiol group of the carboxylic acid can be used as a reactive functionality for the carboxylic acid to become operably bound to the nanocrystal, depending on the composition of the nanocrystal (e.g., to Cd, Zn and the like). Additionally, the carboxylic moiety of the carboxylic acid imparts water solubility to the nanocrystals. Exemplary carboxylic acids may include, but are not limited to, mercaptocarboxylic acid, or mercaptofunctionalized amines (e.g., aminoethanethiol-HCl, or 1-amino-2-methyl-2-propanethiol-HCl).

The present invention provides a fluorescent ink composition, suitable for printing a desired pattern on a substrate, comprising functionalized fluorescent nanocrystals, and an ink carrier. Also provided is a fluorescent ink composition comprising functionalized fluorescent nanocrystals, an ink carrier, and a binder. Also provided is a fluorescent ink composition comprising functionalized fluorescent nanocrystals, an ink carrier, a binder, and one or more additional components suitable for the function of an ink composition. In a preferred embodiment, the functionalized fluorescent nanocrystals are excitable by ultra-violet light, and fluoresce at a spectral wavelength having a peak emission in the range of from about 410 nm to about 900 nm. In a more preferred embodiment, the fluorescence is in the range of visible light.

Functionalized Fluorescent Nanocrystals

As disclosed in detail in U.S. Pat. No. 6,114,038 (the disclosure of which is herein incorporated by reference), fluorescent nanocrystals comprise nanocrystals which have been functionalized by the addition of a plurality of molecules; and preferably, the molecules are selected from an amino acid, a carboxylic acid, and a combination thereof. For example, the nanocrystals may comprise semiconductor nanocrystals that have a core selected from the group consisting of CdSe, CdS, and CdTe (collectively referred to as "CdX"), and may further comprise a passivating shell comprised of YZ wherein Y is Cd or Zn, and Z is S, or Se. Typically, CdX core/YZ shell quantum dots are overcoated with trialkylphosphine oxide, with the alkyl groups most commonly used being butyl and octyl. In one preferred embodiment, the CdX core/YZ shell quantum dots are treated with a large excess of mercaptocarboxylic acid in exchanging the trialkylphosphine oxide coat with a coat comprising a plurality of carboxylic acid molecules. For example, (CdSe)ZnS nanocrystals were prepared in a pyridine solution. The pyridine overcoating of the (CdX) core/YZ shell nanocrystals were exchanged with a carboxylic acid comprising mercaptocarboxylic acid. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. Chloroform was added to precipitate the nanocrystals and wash away excess thiol. The nanocrystals were isolated by centrifugation, washed once more with chloroform, and then washed with hexanes. The residue was briefly dried with a stream of argon. The resultant nanocrystals, coated with molecules of carboxylic acid, were then soluble in water or other aqueous solutions. The nanocrystals, in an aqueous solution, were centrifuged once more, filtered through a 0.2 µm filter, degassed with argon, and stored in an amber vial. The nanocrystals may then be further functionalized by an amino acid comprising a diaminocarboxylic acid. The diaminocarboxylic acid molecules were operably bound to the carboxylic acid molecules of the nanocrystals by using commercially available crosslinking agents and methods known to those skilled in the art. For example, the carboxylic acid-coated nanocrystals were dissolved in an aqueous buffer system (pH of about 7). To the nanocrystals was added EDC (1-ethyl-3-[3-dimethylaminopropyl]carbodiimide). and sulfoNHS (sulfo-N-hydroxysuccinimide) in 500-1000 times excess. The resulting solution was stirred at room temperature for 30 minutes. Mercaptoethanol was added to neutralize unreacted EDC at 20 mM concentration and stirred for 15 minutes. The entire solution was then added dropwise, with stifling, to a solution of a diaminocarboxylic acid comprising lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, fluorescent nanocrystals can be solubilized in an aqueous solution of choice. Once solubilized, the resulting solution can be stored in an amber vial under an inert gas to prevent flocculation. The fluorescent nanocrystals may be operably bound to a successive layer of amino acid molecules by, for example, repeating the procedure and reaction using EDC and sulfoNHS with the amino acid molecules comprising the successive layer.

Similarly, a nanocrystal comprising a doped metal oxide nanocrystal may be operably bound to a plurality of molecules (e.g., a carboxylic acid, and amino acid, or a combination thereof) using methods known in the art. For example, the plurality of molecules having reactive functionalities comprising free carboxyl groups can be chemi-sorbed, adsorbed or otherwise permanently added to the metal oxide portion of the nanocrystal. For example, the metal oxide nanocrystals are suspended in an aqueous solution of an amino acid comprising homocysteine having a pH of about 3.5 for about an hour. The reaction is then stopped by adjusting the pH to neutral, and dialyzing out the aqueous solution.

As an alternative, fluorescent nanocrystals functionalized with a plurality of a sulfur containing amino acid or a seleno containing amino acid. In a preferred embodiment, the fluorescent nanocrystals were functionalized with homocysteine molecules. Nanocrystals (e.g., (CdSe) ZnS) coated with an organic layer (e.g., mercaptoacetic acid) were treated with a molar excess of homocysteine in replacing the organic layer with a coating comprising a plurality of homocysteine molecules. The approximate number of surface Zn sites on the specific size of nanocrystals utilized was calculated. At least a 5 times molar excess of homocysteine (as compared to the number of surface Zn sites) was added to the nanocrystals, as per the following formula. Grams homocysteine=5 (number of Zn surface sites) (volume of solution containing the nanocrystals) (concentration of nanocrystals in solution) (135.2).

The mixture was stirred to dissolve the homocysteine, and then stored at 4° C. for 24 hours. The resultant solution was then centrifuged to remove any precipitate, and the supernatant was transferred to a centrifugal filter for the appropriate volume of supernatant (preferably, with a molecular weight cutoff of about 10 kD or below to retain the fluorescent nanocrystals coated with homocysteine). After centrifugation, and when the desired minimum volume is reached, the fluorescent nanocrystals were then redi1uted in the appropriate aqueous solution (e.g., HEPES buffer) to a volume in which the original mass of homocysteine had been dissolved. The steps of filtering and redilution of the fluorescent nanocrystals in solution may be repeated to improve purity. The resultant fluorescent nanocrystals comprising homocysteine-coated nanocrystals may then be degassed by bubbling with an inert gas, and then stored at 4° C. in an amber bottle.

The functionalized fluorescent nanocrystals used in the fluorescent ink composition according to the present invention are (a) functionalized to be water soluble and to enhance stability in water or a water-based solution; (b) a class of nanocrystals that may be excited with a single excitation light source resulting in detectable fluorescence emissions of high quantum yield and with discrete fluorescence peaks; (c) functionalized so as to have reactive functionalities, such as may be used to operably bind to a binder, if desired; and (d) resistant to photobleaching and fading. "Water-soluble" is used herein to mean sufficiently soluble or dispersible in water or water-based solutions. Preferably, the functionalized fluorescent nanocrystals used in a fluorescent ink composition comprise a substantially uniform size of less than 100 Angstroms, and preferably have a substantially uniform size in the range of from about 2 nm to about 10 nm (diameter). As apparent to one skilled in the art, the amount of the functionalized fluorescent nanocrystals contained within the fluorescent ink composition according to the present invention will depend on factors such as the desired intensity of the emitted fluorescence, the nature of the fluorescent nanocrystals comprising the functionalized fluorescent nanocrystals, the desired viscosity of the fluorescent ink composition, the nature of the substrate onto which is printed the fluorescent ink composition, and the nature of the printer device (e.g., ink jet printer) for which the fluorescent ink composition is intended. In a preferred embodiment, the amount of functionalized fluorescent nanocrystals is in the range of from about 0.0005% to about 5%, based on the total weight of the fluorescent ink composition.

Ink Carrier

Any suitable aqueous-based ink carrier may be used to prepare the fluorescent ink composition according to the present invention. Suitable aqueous-based ink carriers should provide sufficient solubility for the various components of the fluorescent ink composition (e.g., functionalized fluorescent nanocrystals and binder). A suitable aqueous-based ink carrier comprises water (preferably deionized water), or a mixture of water and at least one water-soluble organic solvent. As apparent to one skilled in the art, the selection of the ink carrier will depend on factors such as the desired drying time of the fluorescent ink composition, the desired surface tension and viscosity of the fluorescent ink composition, the nature of the substrate onto which is printed the fluorescent ink composition, and the nature of the printer device (e.g., ink jet printer) for which the fluorescent ink composition is intended. Similarly, depending on such factors, the amount of the ink carrier in the fluorescent ink composition according to the present invention may vary. In a preferred embodiment, the amount of ink carrier is in the range of from about 75% to about 99.5%, based on the total weight of the fluorescent ink composition.

In the case of an aqueous-based ink carrier comprising a mixture of water and at least one water-soluble organic solvent, the amount of water is sufficient for solubilization of the functionalized fluorescent nanocrystals therein. In a preferred embodiment, the aqueous-based ink carrier contains from about 40% to about 95% water (based on total weight of the aqueous-based ink carrier), and more preferably, from about 60% to about 95% water; with the balance being the one or more water-soluble organic solvents. It is further preferred that the water-soluble organic solvent not adversely affect the peak fluorescent emission wavelength or the intensity of the fluorescent emission of excited functionalized fluorescent nanocrystals in the fluorescent ink composition. Water-soluble solvents are known to those skilled in the art to include, but are not limited to, citrus solvents (e.g., citrus peel oils, terpine, terpinene, dipentene, and the like), a polyhydric alcohol (e.g., ethylene glycol, propylene glycol, butylene glycol, triethylene glycol, thiodiglycol, diethylene glycol, hexylene glycol, and the like), an alcohol (e.g., methanol, ethanol, propanol, butanol), a polyalkyl glycol (e.g., polyethylene glycol), alkyl ethers of a polyhydric alcohol, ketones or ketoalcohols, sulfur containing compounds (e.g., dimethyl sulfoxide, tetramethyl sulfone), and esters (e.g., ethylene carbonate, propylene carbonate).

Binder

The fluorescent ink composition may optionally comprise a binder. The binder serves to immobilize, or increase the adhesion of, the fluorescent ink composition to the substrate on which it is printed. The binder is soluble or dispersible in the ink carrier of the fluorescent ink composition, and preferably should not adversely affect the peak fluorescent emission wavelength or the intensity of the fluorescent emission of excited functionalized fluorescent nanocrystals in the fluorescent ink composition. A water-soluble or water-dispersible binder is known to those skilled in the art to include, but is not limited to, one or more of: an acrylic polymer, starch, a polyvinyl alcohol, glycerol, polyethylene glycol, carboxymethylcellulose, hydroxyethyl cellulose, polysodium acrylate, polysodium methacrylate, styrene-acrylic copolymers, styrene-maleic copolymers, pectinic acid, and the like. As apparent to one skilled in the art, the selection and amount of the binder will depend on factors such as the desired surface tension and viscosity of the fluorescent ink composition, the desired water dispersibility, the nature of the substrate onto which is printed the fluorescent ink composition, and the nature of the printer device (e.g., ink jet printer) for which the fluorescent ink composition is intended. In a preferred embodiment, the amount of binder is in the range of from about 1% to about 25%, based on the total weight of the fluorescent ink composition. In a preferred embodiment in which the fluorescent ink composition is used in an ink jet printer, a suitable amount of binder is added to the fluorescent ink composition so as to comprise a viscosity suitable for ink jet printing; i.e., within the range of from about 1 to 20 centiposes (cps), and more preferably, 1.5 to 8 cps.

In a most preferred embodiment, each molecule of binder comprises one or more reactive functionalities that is reactive with (e.g., can be used to operably bind to) one or more reactive functionalities of functionalized fluorescent nanocrystals in forming the fluorescent ink composition according to the present invention. Operably binding the binder to the functionalized fluorescent nanocrystals can result in production of a durable cross-linked fluorescent ink composition that may improve adhesion and surface tension of the fluorescent ink composition to the surface of the substrate onto which it is printed; as well as improving the stability of the fluorescent ink composition in storage and/or printing operation conditions. For example, a molecule of binder comprises one or more free chemical groups, and the functionalized fluorescent nanocrystals each comprise multiple molecules of reactive functionality comprising reactive chemical groups which are capable of becoming operably bound (e.g., ionically) to the reactive functionalities of the binder under suitable conditions so that formed is a fluorescent ink composition comprised of functionalized fluorescent nanocrystals cross-linked with binder. In continuing with an illustrative example, a molecule of binder comprises reactive functionalities comprising amino groups, and the functionalized fluorescent nanocrystals comprise reactive functionalities comprising amino-reactive groups (e.g., carboxyl or amine). In another illustrative example, the binder comprises reactive functionalities comprising carboxyl groups and the functionalized fluorescent nanocrystals comprise reactive functionalities comprising carboxyl-reactive groups (e.g., amine).

Binders having at least one free carboxyl group may include, but are not limited to, carboxylated cellulose derivatives (e.g., carboxyethyl cellulose, carboxypropyl cellulose, carboxymethyl cellulose, hydroxyalkyl celluloses, alkyl celluloses, hydroxypropyl methylcellulose), alginic acid, pectinic acid, esterified starches, polymeric carboxylic acids (e.g., polyacrylic acids, polymethacrylic acids, polymaleic acids), polymeric sulfonic acids, and polycarboxylated vinyl polymers. A preferred binder comprises carboxymethyl cellulose. Binders having at least one amine group may include, but are not limited to, polyethylene glycol end-capped with amine, caseinate, soybean protein, gelatin, polyvinyl amines, polyallylamines, amine-functionalized lignin, amine-functionalized acrylic resins (e.g., dimethyl amino ethyl methacrylate), and amine-functionalized cellulose derivatives (e.g., aminoethylcellulose, aminopropylcellulose). The binder of the fluorescent ink composition according to the present invention may comprise one type or a plurality of types of binders.

In a preferred embodiment, the functionalized fluorescent nanocrystals, ink carrier, and binder comprise at least about 90% by weight of the fluorescent ink composition.

Additional Components

The fluorescent ink composition may comprise an additional component selected from the group consisting of a biocide, a defoamer, a surfactant, a corrosion inhibitor, and a combination thereof. Surfactants may be added to improve the wettability of the fluorescent ink composition to the surface of the substrate onto which it is printed. Surfactants may include, but are not limited to, ethoxylated tetramethyl decynediol, alkylbenzene sulfonates, alkylnaphthyl sulfonates, alcohol sulfates, perfluorinated carboxylic acids, alkylesters of polyethylene glycol, fatty acid esters of glycol, alkylamines, amphoteric surfactants, and a combination thereof. In a preferred embodiment in which the fluorescent ink composition comprises a surfactant as a component, the surfactant may be present in the fluorescent ink composition in an amount of from about 0.01% to about 1.5% by weight of the fluorescent ink composition. A defoamer prevents foaming of the fluorescent ink composition during its preparation, as well as during the printing operation. Any suitable defoamer known to those skilled in the art may be used as an additional component in the fluorescent ink composition according to the present invention; and more preferably, the defoamer is soluble or dispersible in the ink carrier of the fluorescent ink composition. A defoamer may comprise one or more of a mixture of tetramethyldecynediol and propylene glycol, a silicone defoamer, an acetylenic defoamer, and the like. In a preferred embodiment in which the fluorescent ink composition comprises a defoamer as a component, the defoamer may be present in the fluorescent ink composition in an amount of from about 0.5% to about 1.2% by weight of the fluorescent ink composition. A biocide is one or more agents to prevent growth of bacteria, mold, or fungus in the fluorescent ink composition. Any suitable biocide known to those skilled in the art may be used as an additional component in the fluorescent ink composition according to the present invention; and more preferably, the biocide is soluble or dispersible in the ink carrier of the fluorescent ink composition. A suitable biocide may include, but is not limited to, one or more of benzoate salts, sorbate salts, methyl p-hydroxybenzoate, 6-acetoxy-2,2-dimethyl-1,3-dioxane, 1,2-benzisothiazolin-3-one, and the like. In a preferred embodiment in which the fluorescent ink composition comprises a biocide as a component, the biocide may be present in the fluorescent ink composition in an amount of from about 0.02% to about 0.5% by weight of the fluorescent ink composition. A corrosion inhibitor may be added to the fluorescent ink composition to inhibit or reduce corrosion, such as of the metal parts of the printer device (e.g., nozzles or orifices). Any suitable corrosion inhibitor known to those skilled in the art may be used as an additional component in the fluorescent ink composition according to the present invention; and more preferably, the corrosion inhibitor is soluble or dispersible in the ink carrier of the fluorescent ink composition. A suitable corrosion inhibitor may include, but is not limited to, one or more of the 1H-benzotriazoles. In a preferred embodiment in which the fluorescent ink composition comprises a corrosion inhibitor as a component, the corrosion inhibitor may be present in the fluorescent ink composition in an amount of from about 0.01% to about 0.5% by weight of the fluorescent ink composition.

Method of Manufacture

As appreciated by those skilled in the art of inks, the fluorescent ink compositions according to the present invention may be prepared in any number of ways. However, a preferred method of formulating the fluorescent ink compositions comprises mixing the functionalized fluorescent nanocrystals into the aqueous-based ink carrier comprising water or a water-based solution, and then added to and mixed therein is a binder. For fluorescent ink compositions that further comprise one or more additional components (e.g., surfactant, biocide, corrosion inhibitor), the one or more additional components may then be added to and mixed in the fluorescent ink composition. The final mixture may be stirred until a blended, consistent composition is obtained. The fluorescent ink composition may be filtered, if desired, e.g., to remove any impurities.

Printing Devices

As apparent to one skilled in the art of printing, the printing device utilized will depend on the printing method in which the fluorescent ink compositions according to the present invention are applied. In one embodiment, each of a plurality of the fluorescent ink compositions is placed in a separate well of a printing device containing multiple wells for holding ink or ink cartridges, in loading the printing device with fluorescent ink compositions that may be used in combination to print an image. (e.g., security mark or one or more patterns) that is capable of fluorescing in multiple colors when exposed to a single excitation light source suitable for exciting the functionalized fluorescent nanocrystals of the fluorescent ink compositions. The fluorescent inks are printed onto a substrate by the printing device in ratios appropriate to yield the desired colors and to form the desired image. In a preferred embodiment, the printing device is an ink jet printer.

Printing Methods

The fluorescent ink compositions according to the present invention may be used in many printing methods such as ink jet printing, screen printing, gravure printing, letterpress printing, offset printing, relief printing, intaglio printing and the like. As apparent to one skilled in the art, the viscosity of the fluorescent ink compositions will vary depending on the printing method, the printer device, and the substrate onto which the fluorescent ink compositions are printed. For example, a preferred viscosity for ink jet printing may range from about 1.5 to about 15 cps; and more preferably, from about 3 to about 6 cps. In contrast, a preferred viscosity for screen printing may range from about 100 to about 400 cps; and more preferably, from about 200 to about 300 cps. Printed images, generated using the printing method and fluorescent ink compositions according to the present invention, are fluorescent when exposed to an excitation light source (e.g., UV light); and thus become visible or detectable as a color (or colors when more than one fluorescent ink composition is used in the printing method) in the range of from about 410 nm to about 900 nm.

Substrates

The fluorescent ink compositions according to the present invention may be used to print on a number of suitable substrates which may include, but are not limited to, conventional papers (computer paper, currency paper, bond paper, copying paper, image paper), glass, rubber, vinyl, plastics, fabrics, films, inorganic substrates (e.g., metals and woods), and the like. In a preferred embodiment, the substrate comprises a porous or absorbent substrate, such as paper.

Methods for Identification of an Object

As apparent to those skilled in the art from the descriptions herein, one or more of the fluorescent ink compositions of the present invention may be used in a method of providing an object with a security marking for purposes of identification (which may further encompass verification). In one embodiment, a method for identifying an object comprising the steps of:

(a) applying a security mark to the object using a fluorescent ink composition comprising functionalized fluorescent nanocrystals, an aqueous-based ink carrier comprising water or a water-based solution, and a binder;

(b) exposing the object to an excitation light source having a wavelength spectrum in a range of from about 300 nm to about 400 nm;

(c) visualizing the security mark by detecting a peak fluorescent emission in a spectral range of from about 410 nm to about 750 nm; and (d) identifying the object in response to visualizing the security mark.

In another embodiment, a plurality of fluorescent ink compositions are used to apply a security mark to the object, wherein each of the plurality of fluorescent ink compositions is capable of fluorescing a specific (e.g., different than that emitted by any other of the fluorescent ink compositions in the plurality of fluorescent ink compositions) color in providing a security mark which fluoresces in multicolor when visualized; and identification is based on the visualization of the security mark fluorescing in multicolor.

As appreciated by those skilled in the art, the exact components, the proportion of the components, and properties of the components, desired for an ink composition will depend on the application, printing method, and substrate. Therefore, routine experimentation may be required to determine the components and the proportion of the components which are optimum in forming a fluorescent ink composition for a give application and with the desired properties.

Figure 1B:
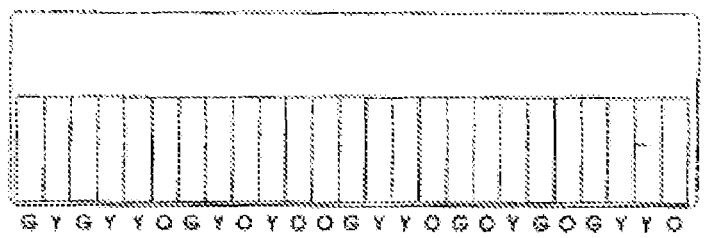
FIG. 1B is a schematic illustration of an identifiable code pattern comprised of separate deposits or localizations of water-soluble quantum dot compounds of different uniform sizes which enable a detectable and identifiable pattern comprised of multiple colors.
Figure 1C:
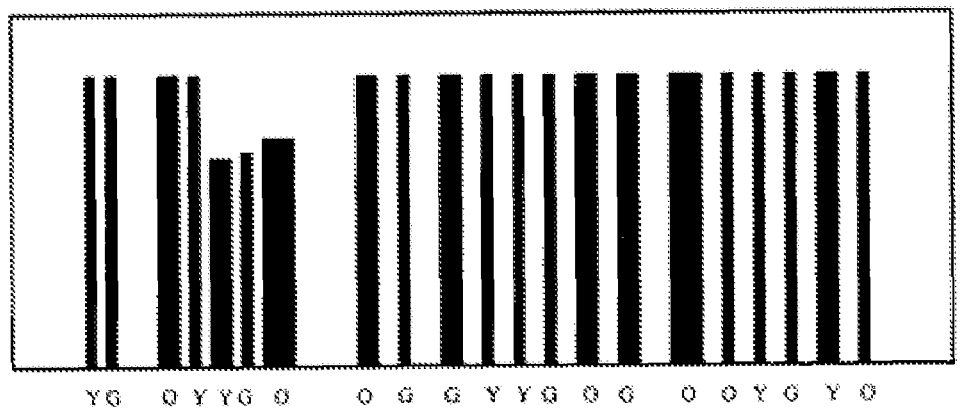
FIG. 1C is another schematic illustration of an identifiable code pattern comprised of separate deposits or localizations of water-soluble quantum dot compounds of different uniform sizes which enable a detectable and identifiable pattern comprised of multiple colors.

In a preferred embodiment of applying an identifiable code pattern to a carrier material, a plurality of water-soluble quantum dot compounds are contacted with the carrier material such that the water-soluble quantum dot compounds becomes associated with the carrier material for the purpose of providing an identifiable code pattern of more than one color. In this embodiment, the plurality of water-soluble quantum dot compounds are contained in separate solutions wherein each solution comprises a suspension of a water-soluble quantum dot compound of a substantially uniform size. Thus, for example, a first solution comprises a suspension of yellow dots; a second solution comprises a suspension of green dots; and a third solution comprises a suspension of orange dots ("first", "second", and "third" are used for the purpose of distinction, and not for the express purpose of designation of order in application). As illustrated in FIGS. 1A, 1B and 1C, each separate solution, when applied to the carrier material, may form a separate deposit or localization of the water-soluble quantum dot compound associated with the carrier material. Thus, for example, the resultant identifiable code pattern may be comprised of separate deposits or localizations of water-soluble quantum dot compounds that enable an identifiable code pattern of multiple colors (see, e.g., FIGS. 1A, 1B, and 1C, wherein "Y" is a deposit or localization of yellow dots; wherein "G" is a deposit or localization of green dots; and wherein "O" is a deposit or localization of orange dots). The separate solutions may either be separately applied to the carrier material, or they may be applied in a simultaneous manner to the carrier material. As illustrated in FIG. 1A, the pattern may take the form of a design, letters, numbers, symbols, or characters. As illustrated in FIG. 1B, the coded pattern may also comprise encoded data, which can be decoded by the detection means in a process of identifying or tracking the carrier material. The encoded data may comprise data matrix symbols, UPC symbols, binary data, alphanumeric data, textual data, numeric data, and data encoded in other formats, any or all of which may be in machine readable format.

The identifiable code pattern comprises deposits or localizations of one or more water-soluble dot compounds that in a pattern that may be made unique to the carrier material to which it is associated; and which can be rendered detectable and readable by exposure of that portion of the carrier material having associated therewith the identifiable code pattern to a light source. Detection of the code pattern after exposure to light may be by detection means comprising a scanner or reader or other analytical instrument which can detect luminescence peaks in the range of about 450 nm to about 700 nm; and, optionally (when the pattern comprises more than one color), distinguish between discrete luminescence peaks within that range. The detection means may further comprise a computer or data processor which can perform one or more functions including, but not limited to, store the detected coded pattern or information decoded therefrom, decode the information represented by the detected coded pattern, compare the detected coded pattern (or information decoded therefrom) to a list or database or entries of coded patterns in a process of verifying or authenticating the detected coded pattern (or information decoded therefrom), and display a warning (e.g., signal or message) if the detected coded pattern is not verified or authenticated. Computer units having some of these functions are known to those skilled in the art (see, e.g., U.S. Pat. No. 5,592,561, the disclosure of which is herein incorporated by reference).

The following examples are provided to further illustrate the present invention, and are not to be construed as limiting the invention in any manner.

Example 1

For purposes of illustration, listed in Table 3 are various examples of a fluorescent ink composition according to the present invention, wherein the fluorescent ink composition comprised functionalized fluorescent nanocrystals, and an ink carrier. The components are listed by their weight percent of the composition; wherein the functionalized fluorescent nanocrystals (e.g., homocysteine-coated fluorescent nanocrystals) are abbreviated as "FNC"; and the ink carrier ("IC") comprised water ($H_2O$) and at least one water soluble organic solvent ("WSO"). The water soluble organic solvents used for purposes of illustration included dimethyl sulfoxide ("DMSO") and polyethylene glycol ("PEG"). The resultant fluorescent ink compositions were printed on a white plain paper substrate (a stock of standard copy paper lacking substantial background fluorescence), and allowed to dry. The print was invisible to the unaided eye. The paper substrate was then exposed to UV light, and the print appeared the appropriate color due to the fluorescence of the fluorescent ink composition used.

TABLE 3

| FNC | IC |
|---|---|
| <1% | $H_2O > 94\%$; DMSO 5% |
| <1% | $H_2O > 59\%$; DMSO 40% |
| <1% | $H_2O > 94\%$; PEG 5% |
| <1% | $H_2O > 59\%$; PEG 40% |

Example 2

For purposes of illustration, listed in Table 4 are various examples of a fluorescent ink composition according to the present invention, wherein the fluorescent ink composition comprised functionalized fluorescent nanocrystals ("FNC"), an ink carrier ("IC"), and a binder. The resultant fluorescent ink compositions were printed on a white plain paper substrate (a stock of standard copy paper lacking substantial background fluorescence), and allowed to dry. The print was invisible to the unaided eye. The paper substrate was then exposed to UV light, and the print appeared the appropriate color due to the fluorescence of the fluorescent ink composition used.

TABLE 4

| FNC | IC | Binder |
|---|---|---|
| <1% | $H_2O > 34\%$; PEG 40% | glycerol 25% |
| <1% | $H_2O > 58\%$; DMSO 40% | glycerol 1% |
| <1% | $H_2O > 58\%$; PEG 40% | glycerol 1% |
| <1% | $H_2O > 93\%$; DMSO 5% | starch 1% |
| <1% | $H_2O > 93\%$; DMSO 5% | gelatin 1% |
| <1% | $H_2O > 58\%$; DMSO 40% | gelatin 1% |

Example 3

For purposes of illustration, listed in Table 5 are various examples of a fluorescent ink composition according to the present invention, wherein the fluorescent ink composition comprised functionalized fluorescent nanocrystals, an ink carrier ("IC"), a binder, and a surfactant. For each composition illustrated in Table 5, functionalized fluorescent nanocrystals were in a weight percent of less than 1%. Illustrative surfactants included triethylamine ("TEA"), and detergent (TRITON; "TTN"). The resultant fluorescent ink compositions were printed on a white plain paper substrate (a stock of standard copy paper lacking substantial background fluorescence), and allowed to dry. The print was invisible to the unaided eye. The paper substrate was then exposed to UV light, and the print appeared the appropriate color due to the fluorescence of the fluorescent ink composition used.

TABLE 5

| IC | Binder | Surfactant |
|---|---|---|
| $H_2O > 92\%$; DMSO 5% | gelatin 1% | 0.01% TEA |
| $H_2O > 92\%$; DMSO 5% | gelatin 1% | 0.1% TEA |
| $H_2O > 92\%$; DMSO 5% | gelatin 1% | 1% TEA |
| $H_2O > 88\%$; DMSO 5% | gelatin 5% | 0.01% TEA |
| $H_2O > 88\%$; DMSO 5% | gelatin 5% | 0.1% TEA |
| $H_2O > 88\%$; DMSO 5% | gelatin 5% | 1% TEA |

TABLE 5-continued

| IC | Binder | Surfactant |
|---|---|---|
| $H_2O > 92\%$; DMSO 5% | gelatin 1% | 0.01% TTN |
| $H_2O > 92\%$; DMSO 5% | gelatin 1% | 0.1% TTN |
| $H_2O > 92\%$; DMSO 5% | gelatin 1% | 1% TTN |
| $H_2O > 88\%$; DMSO 5% | gelatin 5% | 0.01% TTN |
| $H_2O > 88\%$; DMSO 5% | gelatin 5% | 0.1% TTN |
| $H_2O > 92\%$; PEG 5% | gelatin 1% | 1% TEA |
| $H_2O > 92\%$; PEG 5% | gelatin 1% | 1% TTN |

Example 4

The composition according to the present invention comprises water-soluble quantum dots. Desirable features of the quantum dots themselves include that the quantum dots can be excited with a single wavelength of light resulting in a detectable luminescence emission of high quantum yield (e.g., a single quantum dot having at a fluorescence intensity greater than that of at least 10 rhodamine molecules) and with a discrete luminescence peak. The quantum dots typically should have a substantially uniform size of less than 200 Angstroms, and preferably have a substantially uniform size in the range of sizes of from about 1 nm to about 5 nm, or less than 1 nm. Preferred quantum dots are comprised of a core of CdX wherein X is Se or Te or S. Such quantum dots have been previously described in the art (see, e.g., Norris et al., 1996, *Physical Review B*. 53:16338-16346; Nirmal et al., 1996, *Nature* 383:802-804; Empedocles et al., 1996, *Physical Review Letters* 77:3873-3876; Murray et al., 1995, *Science* 270: 1355-1338; Effros et al., 1996, *Physical Review B*. 54:4843-4856; Sacra et al., 1996, *J. Chem. Phys*. 103:5236-5245; Murakoshi et al., 1998, *J. Colloid Interface Sci*. 203: 225-228; Optical Materials and Engineering News, 1995, Vol. 5, No. 12; and Murray et al., 1993, *J. Am. Chem. Soc*. 115:8706-8714; the disclosures of which are hereby incorporated by reference).

Another feature of the quantum dots used in the present invention is that the CdX quantum dots are passivated with an overlayering ("shell") uniformly deposited thereon. The shell is preferably comprised of YZ wherein Y is Cd or Zn, and Z is S, or Se. Quantum dots having a CdX core and a YZ shell have been described in the art (see, e.g., Danek et al., 1996, *Chem. Mater*. 8:173-179; Dabbousi et al., 1997, *J. Phys. Chem. B* 101:9463; Rodriguez-Viejo et al., 1997, *Appl. Phys. Lett*. 70:2132-2134; Peng et al., 1997, *J. Am. Chem. Soc*. 119: 7019-7029; Norris et al., 1996, *Phys. Review B*. 53:16338-16346; Bruchez, Jr. et al., 1998, *Science* 281:2013-2015; Chen and Nie, 1998, *Science* 281:2016-2018; the disclosures of which are hereby incorporated by reference). Another feature of the quantum dots used in the present invention is that they are water-soluble. "Water-soluble" is used herein to mean sufficiently soluble or suspendable in a aqueous-based solution including, but not limited to, water, water-based solutions, buffer solutions, and solutions or liquids used in manufacturing processes, as known by those skilled in the art. Typically, CdX core/YZ shell quantum dots are overcoated with trialkylphosphine oxide, with the alkyl groups most commonly used being butyl and octyl. One method to make the CdX core/YZ shell quantum dots water-soluble is to exchange this overcoating layer with one which will make the quantum dots water-soluble. For example, a mercaptocarboxylic acid is used to exchange with the trialkylphosphine oxide. Exchange of the capping group is accomplished by treating the water-insoluble quantum dots with a large excess of mercaptocarboxylic acid, either neat (e.g., at 60° C.) or in CHCl₃ solution followed by extraction into water. The thiol group of the new capping ligand forms Cd (or Zn)—S bonds, creating a coating which is not easily displaced in solution. This is an improvement over the use of trialkylphosphine oxide, in which the capping ligand form a dative bond between the oxide and the cadmium (or zinc). These ligands are readily displaced in the presence of other Lewis bases such as pyridine. In addition, the carboxylic acid moiety imparts water solubility to the quantum dots. Quantum dots capped with trialkylphosphine oxide are soluble only in organic, non-polar (or weakly polar) solvents. Another method to make the CdX core/YZ shell quantum dots water-soluble is by the formation of a layer of silica around the dots (Bruchez et al., 1998, supra). An extensively polymerized polysilane shell imparts water solubility to nanocrystalline materials, as well as allowing further chemical modifications of the silica surface. Another method to make CdX core/YZ shell quantum dots water-soluble is to overcoat the quantum dots with mercapto-functionalized amines (e.g., aminoethanethiol-HCl, homocysteine, or 1-amino-2-methyl-2-propanethiol-HCl). Preferably, these water-soluble quantum dots, before being functionalized, have a substantially uniform size in the range of sizes of a minimum of from less than or equal to about 1 nm, to a maximum of about 20 nm.

As known to those skilled in the art, the absorbance peak and fluorescence peak emission of the quantum dots depends on such factors which include, but are not limited to, the chemical nature of the quantum dot, and the size of the core/shell quantum dot. For example, CdSe/ZnS quantum dots having a diameter of about 68.4 angstroms (Å) may be excited with light of a wavelength in the range of from about 400 nm to 500 nm, and emit a luminescence peak (orange) at 609 nm which may be detected using appropriate detection means. CdSe/ZnS quantum dots having a diameter of about 53.2 Å may be excited with light of a wavelength in the range of from about 400 nm to 500 nm, and emit a luminescence peak (yellow) at 545 nm which may be detected using appropriate detection means. CdSe/ZnS quantum dots having a diameter of about 46.6 Å may be excited with light of a wavelength in the range of from about 400 nm to 500 nm, and emit a luminescence peak (green) at 522 nm which may be detected using appropriate detection means. For purposes of brevity of description only, and not limitation, water-soluble quantum dots or functionalized quantum dots that emit a luminescence peak ranging from about 585 nm to about 635 nm may be referred to herein as "orange dots", water-soluble quantum dots or functionalized quantum dots that emit a luminescence peak ranging from about 520 nm to about 570 nm may be referred to herein as "yellow dots"; and water-soluble quantum dots or functionalized quantum dots that emit a luminescence peak ranging from about 495 nm to about 545 nm may be referred to herein as "green dots".

Example 5

In this example, illustrated are embodiments for functionalizing water-soluble quantum dots with one or more reactive functionalities. In a first method, water-soluble quantum dots with a carboxylate-terminated capping group are operably linked to a protein using a compound which facilitates a chemical association or bond formation between the water-soluble quantum dot and a protein (e.g., reactive towards both $NH_2$ and $CO_2H$). One such compound is 1-[3-(dimethylamino) propyl]-3-ethylcarbodiimide hydrochloride ("EDC") which functions to activate at least one reactive functionality (e.g., a carboxylate) to catalyze its reaction with another reactive functionality such as the amide group of a protein (the term "protein" also encompasses a peptide). For example, upon reaction of the EDC-activated carboxylate with an amide of a protein, the EDC is precipitated from the reaction in the form of urea. As apparent to those skilled in the art, the protein has no particular size, length or content limitations, so long as the protein can function to operably link to the carrier material desired to be linked. Such proteins will be apparent to those skilled in the art to include, but are not limited to, avidin, streptavidin, and their biotin-binding derivatives/modified versions (e.g., neutravidin, nitro-avidin, nitro-streptavidin, aceylated avidin, and the like). For purposes of brevity of description, but not limitation, avidin or streptavidin or their biotin-binding derivatives/modified versions will be referred to hereinafter as "avidin". In an illustrative embodiment, water-soluble quantum dots were formed by coating with 11-mercaptoundecanoic acid, and deprotonating with potassium-t-butoxide. The carboxylated quantum dots were then esterified by treatment with EDC followed by sulfo-N-hydroxy-succinimide (sNHS). These quantum dots were then contacted with avidin under sufficient conditions to form an amide bond between the EDC-activated carboxylate of the quantum dot and the amine groups on avidin; thereby forming avidinylated, water-soluble quantum dots. The avidinylated, water-soluble quantum dots can then be contacted with and operably linked to a carrier molecule having one or more free biotin molecules (including native biotin or a biotin derivative having avidin-binding activity; e.g., biotin dimers, biotin multimers, carbobiotin, and the like). Using methods known to those skilled in the art, biotin molecules can be added to or incorporated by derivatization of the protein via lysine e-amino groups, or via thiol groups generated by reduction of cysteines (see, e.g., U.S. Pat. No. 5,756,685).

In another embodiment, the functionalized quantum dots of the present invention are produced using reactive functionalities comprising thiol group and thiol reactive groups. One illustration of this embodiment involves use of maleimide derivatives. For example, CdX core/YZ shell quantum dots are overcoated with mercapto-functionalized amines (e.g., aminoethanethiol-HCl, homocysteine, or 1-amino-2-methyl-2-propanethiol-HCl). Thus, the overcoating comprises a cap with amino groups. To these amino group-capped quantum dots are added (either in the presence or absence of EDC) a maleimide derivative that reacts with amino groups. Such a maleimide derivative may include, but is not limited to 3-maleimidopropionic acid N-hydroxysuccinimide ester, 3-maleimidopropionic acid, 3-maleimido-benzoic acid N-hydroxysuccinimide ester, 4-(maleimido-methyl)-1-cyclohexanecarboxylic acid N-hydroxysuccinimide ester. The resultant quantum dots, having a thiol-reactive group, can interact with and bind to carrier materials having been previously derivatized with one or more thiol groups. The resultant quantum dots, having a thiol-reactive group, can interact with and form thioether bonds in operably linking to the carrier material having one or more thiol groups. A carrier material comprising protein may be derivatized to contain one or thiol-reactive groups using methods known to those skilled in the art. In one method, a hetero-bifunctional crosslinking reagent (e.g., SMCC-succinimidyl 4-(N-maleimidomethyl)cyclohexane-1-carboxylate; or SPDP (succinimidyl 3-(2-pyridyldithio)propionate) can introduce thiol-reactive groups in a protein (see, e.g., U.S. Pat. Nos. 5,672,683, and 5,256,395; the disclosures of which are herein incorporated by reference).

In another embodiment, the functionalized quantum dots of the present invention are produced utilizing reactive functionalities comprising amino groups and amino reactive groups. One illustration of this embodiment involves overcoating CdX core/YZ shell quantum dots with mercapto-functionalized amines (e.g., aminoethane-thiol-HCl, homocysteine, or 1-amino-2-methyl-2-propanethiol-HCl). Thus, the overcoating comprises a cap with amino groups. To these amino group-capped quantum dots are contacted, and operably linked, a carrier material which has been previously derivatized with one or more amino reactive groups. Amino reactive groups are known to those skilled in the art to include, but are not limited to, active ester groups, haloacetyl groups, azide groups, isocyanate groups, isothiocyanate groups, and acid anhydride groups (see, e.g., U.S. Pat. No. 5,580,923, the disclosure of which is herein incorporated by reference).

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

The invention claimed is:

1. An image formed by a method comprising applying onto a substrate a fluorescent ink composition, wherein the composition comprises functionalized fluorescent semiconductor nanocrystals, an aqueous-based ink carrier comprising water or a water-based solution, and a binder, wherein the method provides an image on a substrate for subsequent identification.

2. An image formed by the method according to claim 1, wherein the image comprises a security mark.

3. An image formed by the method according to claim 1, wherein the fluorescent ink composition further comprises an additional component selected from the group consisting of a biocide, a surfactant, a defoamer, a corrosion inhibitor, and a combination thereof.

4. An image formed by the method according to claim 1, wherein the method further comprises applying onto the substrate a plurality of fluorescent ink compositions wherein each of the plurality of fluorescent ink compositions is capable of fluorescing a specific color, thereby providing an image which is multicolor upon subsequent identification.

5. An image formed by the method according to claim 1, wherein the functionalized fluorescent nanocrystals are operably bound to the binder, thereby forming a cross-linked fluorescent ink composition.

6. A substrate having printed thereon an image according to claim 1.

7. A substrate having printed thereon an image according to claim 2.

8. A substrate having printed thereon an image according to claim 3.

9. A substrate having printed thereon an image according to claim 4.

10. A substrate having printed thereon an image according to claim 5.

* * * * *